(12) United States Patent
Hutchins et al.

(10) Patent No.: US 7,433,880 B2
(45) Date of Patent: Oct. 7, 2008

(54) METHOD AND SYSTEM FOR HIGH SPEED ENCODING, PROCESSING AND DECODING OF DATA

(75) Inventors: Vondal C. Hutchins, Cisco, TX (US); Joyce Hutchins, Cisco, TX (US)

(73) Assignee: Atwell Computer Medical Innovations, Inc., Cisco, TX (US)

( * ) Notice: Subject to any disclaimer, the term of this patent is extended or adjusted under 35 U.S.C. 154(b) by 363 days.

(21) Appl. No.: 10/939,920

(22) Filed: Sep. 13, 2004

(65) Prior Publication Data

US 2006/0059181 A1   Mar. 16, 2006

(51) Int. Cl.
*G06F 17/30* (2006.01)
(52) U.S. Cl. .......................................... 707/101; 714/1
(58) Field of Classification Search ................. 707/101, 707/200, 8
See application file for complete search history.

(56) References Cited

U.S. PATENT DOCUMENTS

| | | | | | |
|---|---|---|---|---|---|
| 4,597,057 | A | * | 6/1986 | Snow | 341/60 |
| 5,021,782 | A | * | 6/1991 | Perron et al. | 341/67 |
| 5,225,833 | A | * | 7/1993 | Fisher et al. | 341/90 |
| 5,327,341 | A | * | 7/1994 | Whalen et al. | 705/3 |
| 5,551,020 | A | * | 8/1996 | Flax et al. | 707/101 |
| 5,642,731 | A | * | 7/1997 | Kehr | 600/300 |
| 6,233,580 | B1 | * | 5/2001 | Kaplan et al. | 707/101 |
| 6,714,145 | B1 | * | 3/2004 | Marques | 341/50 |
| 2002/0065854 | A1 | * | 5/2002 | Pressly | 707/530 |
| 2002/0143521 | A1 | * | 10/2002 | Call | 704/1 |
| 2003/0036683 | A1 | * | 2/2003 | Kehr et al. | 600/300 |
| 2005/0071192 | A1 | * | 3/2005 | Milosavljevic | 705/2 |
| 2005/0251417 | A1 | * | 11/2005 | Malhotra et al. | 705/2 |

OTHER PUBLICATIONS

US Certificate of Registration, Copyright Serial No. TXu-028-144, Authors Vondal C. Hutchins and Joyce M. Hutchins, Computer Program, Nov. 26, 2001.

* cited by examiner

*Primary Examiner*—Joon Hwang
*Assistant Examiner*—SyLing Yen
(74) *Attorney, Agent, or Firm*—Gardere Wynne Sewell, LLP; Karl L. Larson

(57) ABSTRACT

A system, method and computer program for processing data having a plurality of data values contained in a plurality of data fields of varying types and lengths that includes encoding data values of the data fields into integer values, forming one or more first binary words from the binary form of the integer values, identifying a selected combination of the data fields, unpacking integer values of encoded data values of the identified data fields from the one or more first binary words, combining the unpacked integer values to form one or more second binary words, and employing each of the one or more second binary words as an input parameter to a selected function to derive output information collectively representing data values of the identified data fields. At least some portion of at least one of the one or more first binary words are formed from the binary form of the integer values encoded from at least two different data fields.

27 Claims, 14 Drawing Sheets

| | DATA ELEMENT | MAX NUMBER | BITS | RANK | BINARY |
|---|---|---|---|---|---|
| 260 | DRG (243) | 540 | 10 | 243 | 0011110011 |
| 262 | Diagnosis3 (25000) | 15535 | 14 | 2452 | 00100110010100 |
| 264 | LengthOfStay (84) | 255 | 8 | 84 | 01010100 |

| | | BINARY |
|---|---|---|
| 266 | word = Diagnosis3 | 00000000000000000000100110010100 |
| 268 | word <<= 10 | 00000000001001100101000000000000 |
| 270 | word += DRG | 00000000001001100101000011110011 |
| 272 | word <<= 8 | 00100110010100001111001100000000 |
| 274 | word += LengthOfStay | 00100110010100001111001101010100 |

| Name | OverFlow | Def | Word | Bits | Dec | Shift | Add | Type | Key |
|---|---|---|---|---|---|---|---|---|---|
| SEX, | 0, | 5, | 0, | 2, | 0, | 30, | 0, | A, | N |
| SSN, | 0, | 0, | 0, | 30, | 0, | 0, | 9, | I, | N |
| ProvSSN, | 0, | 0, | 1, | 30, | 0, | 2, | 9, | I, | N |
| Blood, | 0, | 21, | 1, | 1, | 0, | 1, | 0, | A, | N |
| Autospy, | 0, | 21, | 1, | 1, | 0, | 0, | 0, | A, | N |
| RegisterNum, | 0, | 0, | 2, | 24, | 0, | 8, | 0, | I, | S |
| ClinSvcDays, | 255, | 0, | 2, | 8, | 0, | 0, | 4, | I, | N |
| HospCost, | 2097151, | 0, | 3, | 21, | 2, | 11, | 10, | F, | M |
| ▸DRG, | 0, | 3, | 3, | 10, | 0, | 1, | 0, | A, | N |
| HCFA_CC, | 0, | 21, | 3, | 1, | 0, | 0, | 0, | A, | N |
| ProvCost, | 524287, | 0, | 4, | 19, | 2, | 13, | 10, | F, | M |
| DateAdmission, | 0, | 0, | 4, | 13, | 0, | 0, | 1995, | D, | N |
| ▸Diagnosis3, | 0, | 1, | 5, | 14, | 0, | 18, | 0, | A, | D |
| ZIP, | 0, | 0, | 5, | 17, | 0, | 1, | 0, | I, | N |
| SurgicalCase, | 0, | 21, | 5, | 1, | 0, | 0, | 0, | A, | N |
| Birthday, | 0, | 0, | 6, | 16, | 0, | 14, | 1890, | D, | N |
| Diagnosis4, | 0, | 1, | 6, | 14, | 0, | 0, | 0, | A, | D |
| Diagnosis5, | 0, | 1, | 7, | 14, | 0, | 18, | 0, | A, | D |
| Diagnosis2, | 0, | 1, | 7, | 14, | 0, | 4, | 0, | A, | D |
| SurgNum, | 15, | 0, | 7, | 4, | 0, | 0, | 2, | I, | C |
| Diagnosis1, | 0, | 1, | 8, | 14, | 0, | 18, | 0, | A, | D |
| Num_CC_Coded, | 0, | 0, | 8, | 4, | 0, | 14, | 0, | I, | N |
| DX_CC_HCFA, | 0, | 1, | 8, | 14, | 0, | 0, | 0, | A, | D |
| Diagnosis8, | 0, | 1, | 9, | 14, | 0, | 18, | 0, | A, | D |
| DxNum, | 15, | 0, | 9, | 4, | 0, | 14, | 2, | I, | B |
| Diagnosis6, | 0, | 1, | 9, | 14, | 0, | 0, | 0, | A, | D |
| UnderlyingCause, | 0, | 1, | 10, | 14, | 0, | 17, | 0, | A, | N |
| Diagnosis7, | 0, | 1, | 10, | 14, | 0, | 3, | 0, | A, | D |
| Race, | 0, | 6, | 10, | 3, | 0, | 0, | 0, | A, | N |
| SurgProcedure8, | 0, | 2, | 11, | 13, | 0, | 19, | 0, | A, | Q |
| ICUDays, | 63, | 0, | 11, | 6, | 0, | 13, | 3, | I, | N |
| DateDischarge, | 0, | 0, | 11, | 13, | 0, | 0, | 1995, | D, | N |
| SurgProcedure7, | 0, | 2, | 12, | 13, | 0, | 19, | 0, | A, | Q |
| Hosp, | 0, | 34, | 12, | 6, | 0, | 13, | 0, | A, | P |
| SurgProcedure6, | 0, | 2, | 12, | 13, | 0, | 0, | 0, | A, | Q |
| MDC, | 0, | 37, | 13, | 5, | 0, | 26, | 0, | A, | N |
| SurgProcedure5, | 0, | 2, | 13, | 13, | 0, | 13, | 0, | A, | Q |
| SurgProcedure4, | 0, | 2, | 13, | 13, | 0, | 0, | 0, | A, | Q |
| Ethnic, | 0, | 35, | 14, | 3, | 0, | 29, | 0, | A, | N |
| Admission, | 0, | 30, | 14, | 3, | 0, | 26, | 0, | A, | N |
| SurgProcedure2, | 0, | 2, | 14, | 13, | 0, | 13, | 0, | A, | Q |
| SurgProcedure3, | 0, | 2, | 14, | 13, | 0, | 0, | 0, | A, | Q |
| Discharge, | 0, | 10, | 15, | 3, | 0, | 29, | 0, | A, | N |
| SurgProcedure1, | 0, | 2, | 15, | 13, | 0, | 16, | 0, | A, | Q |
| ProvSpecialty, | 0, | 36, | 15, | 8, | 0, | 8, | 0, | A, | N |
| ▸LengthOfStay, | 255, | 0, | 15, | 8, | 0, | 0, | 4, | I, | N |
| BassinetDays, | 127, | 0, | 16, | 7, | 0, | 14, | 4, | I, | N |
| ICUDays, | 127, | 0, | 16, | 7, | 0, | 7, | 4, | I, | N |
| ClinicService, | 0, | 40, | 16, | 7, | 0, | 0, | 0, | A, | N |
| DiagnosisInc, | 0, | 1, | 0, | 14, | 0, | 0, | 0, | A, | E |
| SurgProcedureInc, | 0, | 2, | 0, | 13, | 0, | 0, | 0, | A | G |

Figure 10

| | DATA ELEMENT | MAX NUMBER | BITS | RANK | BINARY |
|---|---|---|---|---|---|
| 260 | DRG (243) | 540 | 10 | 243 | 0011110011 |
| 262 | Diagnosis3 (25000) | 15535 | 14 | 2452 | 00100110010100 |
| 264 | LengthOfStay (84) | 255 | 8 | 84 | 01010100 |

| | | BINARY |
|---|---|---|
| 266 | word = Diagnosis3 | 000000000000000000100110010100 |
| 268 | word <<= 10 | 000000000100110010100000000000 |
| 270 | word += DRG | 000000000100110010100011110011 |
| 272 | word <<= 8 | 00100110010100011100110000000 |
| 274 | word += LengthOfStay | 00100110010100011100110101010100 |

Figure 11

|  | BINARY |
|---|---|
| 276 — mask1=pow( 2,14) -1 | 00000000000000000011111111111111 |
| 278 — mask2=pow( 2,10) -1 | 00000000000000000000001111111111 |
| 280 — mask3=pow( 2, 8) -1 | 00000000000000000000000011111111 |

|  | BINARY |
|---|---|
| 282 — word | 00100110010100001111001101010100 |
| 284 — LengthOfStay = (word >> 0) | 00100110010100001111001101010100 |
| 286 — LengthOfStay &= mask3 | 00000000000000000000000001010100 |
| 288 — DRG = (word >> 8) | 00000000001001100101000011110011 |
| 290 — DRG &= mask2 | 00000000000000000000000011110011 |
| 292 — Diagnosis3 = (word >> 18) | 00000000000000000000100110010100 |
| 294 — Diagnosis3 &= mask1 | 00000000000000000000100110010100 |

```
           Covered Charges for Medicare Inpatients
                       By Sex and Age
                  500000 Sample FY 2002

/ - - - - - - MedParIn_db - - - - - /
                                    CoveredCharges SEX        AGE        NUMBER      MEAN       TOTAL        S.D.
                          ------      ----       -----        ----

MALE       < 25           625     16030      10018964     27234
    MALE       25-44        12089     15899     192200444     27085
    MALE       45-64        33888     20943     709706304     38558
    MALE       65-69        37013     23641     875007487     36223
    MALE       70-74        39153     22916     897245953     31003
    MALE       75-79        38889     22932     891809113     32977
    MALE       80-84        31093     21245     660570042     30042
    MALE       85-89        17526     19375     339558407     26249
    MALE       90+           8267     16497     136381942     20153
    FEMALE     < 25           694     17223      11952928     29898
    FEMALE     25-44        11060     16386     181223671     29249
    FEMALE     45-64        33558     19419     651676851     36180
    FEMALE     65-69        39885     20490     817250538     31738
    FEMALE     70-74        45113     19778     892225580     29047
    FEMALE     75-79        50664     19665     996296941     28100
    FEMALE     80-84        46309     18579     860352643     24329
    FEMALE     85-89        32707     16873     551860208     19543
    FEMALE     90+          21467     14595     313312621     14668

Total       500000     19977    9988650637     29949

DATABASE  c:\Program Files\acmi\acmi2\data\MedParIn_db 2002
CLASSIFY  SEX ALL
CLASSIFY  AGE ALL
DEPENDENT CoveredCharges >-1

Records read         = 500000
Records selected     = 500000
Records in report    = 500000
Process records time(sec) = 1
Generate report time(sec) = 0
             Total time(sec) = 1
```

```
021    TULAREMIA
0210   ULCEROGLANDUL TULAREMIA
0211   ENTERIC TULAREMIA
0219   TULAREMIA NOS
022    ANTHRAX
0220   CUTANEOUS ANTHRAX
0221   PULMONARY ANTHRAX
0222   GASTROINTESTINAL ANTHRAX
023    BRUCELLOSIS
0230   BRUCELLA MELITENSIS
0238   BRUCELLOSIS NEC
0239   BRUCELLOSIS NOS
024    GLANDERS
025    MELIOIDOSIS
026    RAT-BITE FEVER
0260   SPIRILLARY FEVER
0261   STREPTOBACILLARY FEVER
0269   RAT-BITE FEVER NOS
027    OTH ZOONOTIC BACTERL DIS
0270   LISTERIOSIS
0271   ERYSIPELOTHRIX INFECTION
0279   ZOONOTIC BACT DIS NOS
030    LEPROSY
0300   LEPROMATOUS LEPROSY
0301   TUBERCULOID LEPROSY
03282  DIPHTHERITIC MYOCARDITIS
03289  DIPHTHERIA NEC
0329   DIPHTHERIA NOS
033    WHOOPING COUGH
0330   BORDETELLA PERTUSSIS
0331   BORDETELLA PARAPERTUSSIS
0338   WHOOPING COUGH NEC
034    STREP SORE THR/SCARLATNA
0340   STREP SORE THROAT
0341   SCARLET FEVER
035    ERYSIPELAS
036    MENINGOCOCCAL INFECTION
V4389  ORGAN/TISS REPLACMNT NEC
V44    ARTIFICIAL OPENNG STATUS
V440   TRACHEOSTOMY STATUS
V441   GASTROSTOMY STATUS
```

298

24B

```
001 CRANIOTOMY AGE >17 W CC
002 CRANIOTOMY AGE >17 W/O CC
003 CRANIOTOMY AGE 0-17
004 NO LONGER VALID
005 NO LONGER VALID
006 CARPAL TUNNEL RELEASE
007 PERIPH & CRANIAL NERVE & OTHER NERV SYST PROC W CC
008 PERIPH & CRANIAL NERVE & OTHER NERV SYST PROC W/O CC
009 SPINAL DISORDERS & INJURIES
044 ACUTE MAJOR EYE INFECTIONS
045 NEUROLOGICAL EYE DISORDERS
046 OTHER DISORDERS OF THE EYE AGE >17 W CC
047 OTHER DISORDERS OF THE EYE AGE >17 W/O CC
048 OTHER DISORDERS OF THE EYE AGE 0-17
049 MAJOR HEAD & NECK PROCEDURES
050 SIALOADENECTOMY
051 SALIVARY GLAND PROCEDURES EXCEPT SIALOADENECTOMY
052 CLEFT LIP & PALATE REPAIR
055 MISCELLANEOUS EAR, NOSE, MOUTH & THROAT PROCEDURES
056 RHINOPLASTY
057 T&A PROC,EXC TONSLECTOMY &/OR ADENOIDECT ONLY,AGE >17
058 T&A PROC,EXC TONSLECTMY &/OR ADENOIDECT ONLY,AGE 0-17
059 TONSILLECTOMY &/OR ADENOIDECTOMY ONLY, AGE >17
060 TONSILLECTOMY &/OR ADENOIDECTOMY ONLY, AGE 0-17
110 MAJOR CARDIOVASCULAR PROCEDURES W CC
111 MAJOR CARDIOVASCULAR PROCEDURES W/O CC
112 NO LONGER VALID
113 AMPUTATION FOR CIRC SYST DISD EXCEPT UPPER LIMB & TOE
114 UPPER LIMB & TOE AMPUTATION FOR CIRC SYSTEM DISORDERS
540 LYMPHOMA & LEUKEMIA W MAJOR OR PROCEDURE W/O CC
```

Figure 14

METHOD AND SYSTEM FOR HIGH SPEED ENCODING, PROCESSING AND DECODING OF DATA

BACKGROUND OF THE INVENTION

1. Field of the Invention

The present invention relates to a system, method, and computer program for encoding, processing and decoding data that provides for enhanced speed and efficiency. More particularly, the present invention relates to a system, method, and computer program for encoding, processing and decoding a large volume of data having different types of data fields, arranged as collections of data values of varying length, that is stored and readily accessible from storage for use in the preparation of reports.

2. Discussion of the Background

In fields where a large volume of data is processed, such as the healthcare field, there is a continuing need to store a large volume of data that may have many different types or categories of data fields. For example, in the healthcare field, different data categories for respective patients may include diagnosis related data, procedures performed, inpatient length of stay and cost information. Further, other data categories may include the patent's age, ethnic and gender information. Hereinafter, a data field is used to describe a collection of data values, such as the column name for a column of data in a row-column table or database. It is frequently necessary to access the data related to these data fields after the data has been stored, such as generating reports that combine portions of data selected from different types of data fields.

Data fields tend to vary in both data size and data type. A data type, for instance, may be, but is not limited to, numeric, alphanumeric, date, and currency. For example, cost and length of stay information may be represented as numerical values. Whereas, diagnoses, diagnosis related groups (DRG) and medical procedures may be represented as alphanumerical codes that identify particular diagnoses or procedures, respectively. Further, the size of a data field may vary depending on the maximum numerical value associated with the data field. Additionally, some types of data fields may be used as independent variables, while other types serve as dependent variables. An independent variable is defined as any variable for which counts are computed for each data value or group of values. Further, a dependent variable is defined as any variable for which meaningful statistics are computed for each independent variable or combination of independent variables. For example, in an important class of reports, independent variables may represent age, gender, diagnoses and procedures. Whereas, dependent variables may represent statistics, such as the length of stay and cost information that are calculated based on selected age, gender, diagnoses and/or procedures.

Differences among respective types of data fields tend to impede efforts to efficiently store and access different data types in a common storage arrangement. In providing improved storage and access for such data, it is important to ensure that users will be able to readily generate reports of different kinds, each comprising a different combination of available stored data fields.

SUMMARY OF THE INVENTION

Accordingly, one object of the present invention is to provide a method for processing data having a plurality of data values contained in a plurality of data fields of varying types and lengths. The method includes encoding data values of the data fields into integer values, forming one or more first binary words from the binary form of the integer values, and identifying a selected combination of the data fields. The method further includes unpacking integer values of encoded data values of the identified data fields from the one or more first binary words, combining the unpacked integer values to form one or more second binary words, and employing each of the one or more second binary words as an input parameter to a selected function to derive output information collectively representing data values of the identified data fields. At least some portion of at least one of the one or more first binary words are formed from the binary form of the integer values encoded from at least two different data fields.

Another object of the present invention is to provide a method for encoding a plurality of data values contained in a plurality of data fields of varying types and lengths. The data values in one of the plurality of data fields are different in at least one of number, type and length from the data values in at least one other of the plurality of data fields. The method includes mapping each of the plurality of data values of a corresponding one of the plurality of data fields to an integer value in a corresponding plurality of integers, representing each integer value in one of the plurality of integers as a binary having a bit length determined by the largest integer value in the one of the plurality of integers, and combining respective binaries to form one or more binary words. Each of the one or more binary words are of the same specified length, and the binaries contained in at least one of the one or more binary words represents data values selected from different data fields.

Yet another object of the present invention is to provide a computer program for processing data having a plurality of data values contained in a plurality of data fields of varying types and lengths. The computer program includes a first computer code for encoding data values of the data fields into integer values, a second computer code for forming one or more first binary words from the binary form of the integer values, and a third computer code for identifying a selected combination of the data fields. The computer program further includes a fourth computer code for unpacking integer values of encoded data values of the identified data fields from the one or more first binary words, a fifth computer code for combining the unpacked integer values to form one or more second binary words, and a sixth computer code for employing each of the one or more second binary words as an input parameter to a selected function to derive output information collectively representing data values of the identified data fields. At least some portion of at least one of the one or more first binary words are formed from the binary form of the integer values encoded from at least two different data fields.

Still another object of the present invention is to provide a computer system for processing data having a plurality of data values contained in a plurality of data fields of varying types and lengths. The computer system includes a processor and a computer readable medium connected to the processor. The computer-readable medium includes processor instructions configured to be read by the processor and to thereby cause the processor to encode data values of the data fields into integer values, form one or more first binary words from the binary form of the integer values, and identify a selected combination of the data fields. Further, the processor is caused to unpack integer values of encoded data values of the identified data fields from the one or more first binary words, combine the unpacked integer values to form one or more second binary words, and employ each of the one or more second binary words as an input parameter to a selected function to derive output information collectively representing data values of the identified data fields. At least some portion of at least one of the one or more first binary words are formed from the binary form of the integer values encoded from at least two different data fields.

BRIEF DESCRIPTION OF THE DRAWINGS

A more complete appreciation of the present invention and many of the attendant advantages thereof will be readily obtained as the same becomes better understood by reference to the following detailed description when considered in conjunction with the accompanying drawings, wherein:

FIG. 10 is an example of an encoded dictionary file according to an embodiment of the present invention;

FIG. 11 is an example of packing a binary word according to an embodiment of the present invention;

FIG. 12 is an example of extracting data fields from a binary word according to an embodiment of the present invention;

FIG. 13 is an example of a generated report according to an embodiment of the present invention; and FIG. 14 provides examples of definition files according to an embodiment of the present invention.

DETAILED DESCRIPTION OF THE PREFERRED EMBODIMENTS

Figure 1:
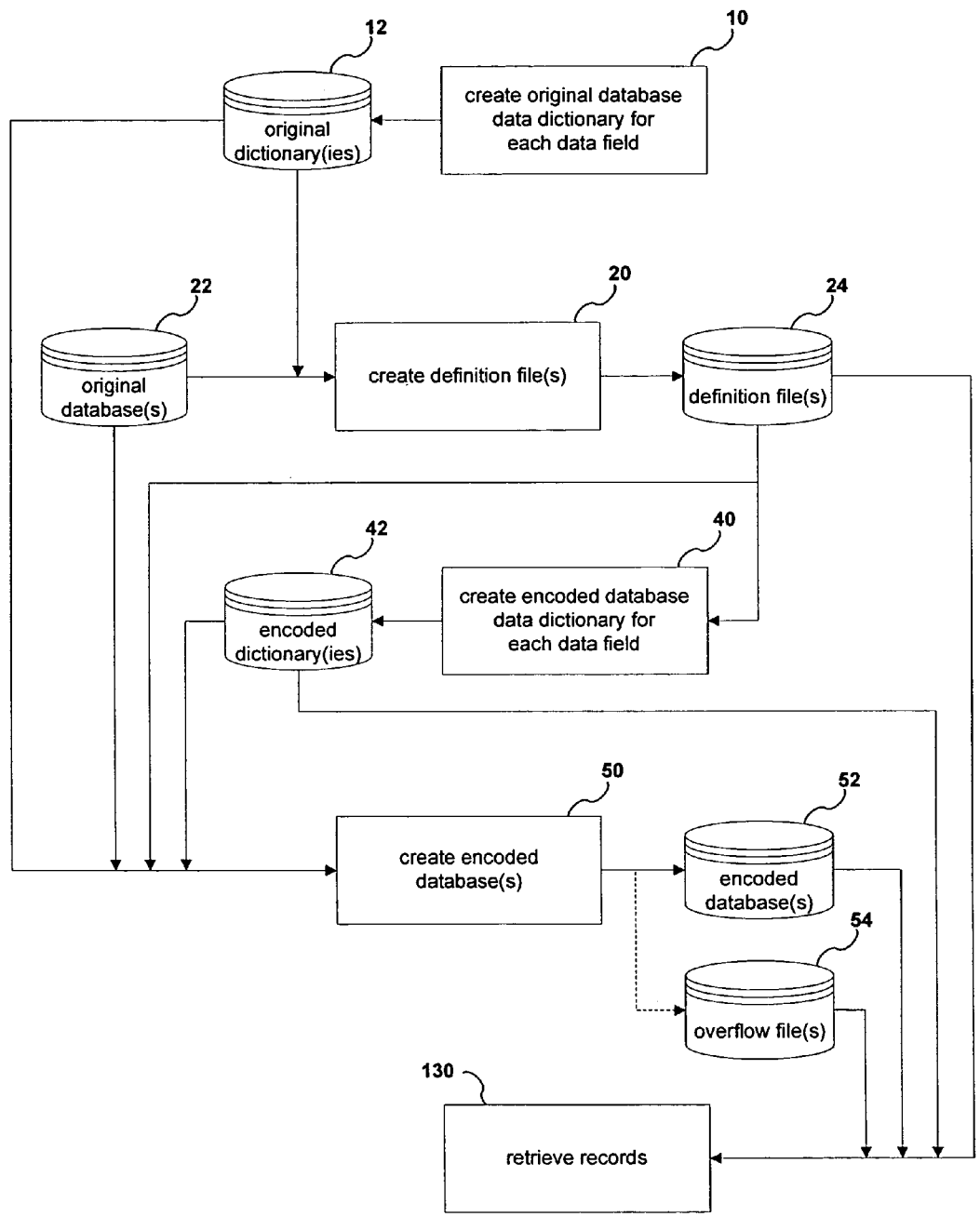
FIG. 1 is a flow chart illustrating an overview of a method and system for high speed encoding, processing and decoding of data according to an embodiment of the present invention.

Referring now to the drawings, wherein like reference numerals designate identical or corresponding parts throughout the several views, preferred embodiments of the present invention are described.

Referring to FIG. 1, a flow chart illustrating an overview of a method and system for high speed encoding, processing and decoding of data according to an embodiment of the present invention is shown. Generally, the method and system for high speed encoding, processing and decoding of data uses one or more original dictionaries 12 and one or more encoded dictionaries 42 to generate an encoded form of one or more original dictionaries 12. The encoded form of the one or more original dictionaries 12 includes, but is not limited to, one or more definition files 24, one or more encoded databases 52, and possibly one or more overflow files 54. The creation of one or more definition files 24 that specify distinct textual information relative to data defined as an alphanumeric data type is shown generally at block 20 of FIG. 1 and discussed in detail below with reference to FIG. 2. Further, the creation of one or more encoded databases 52 along with one or more overflow files 54 is shown generally at block 50 of FIG. 1 and discussed in detail below with reference to FIGS. 3-5. Finally, the encoded form (24, 52 and 54) of one or more original dictionaries 12 is used to optimally process and decode data records as shown generally at block 130 of FIG. 1 and discussed in detail below with reference to FIGS. 6-9.

As shown at block 10 of FIG. 1, one or more original dictionaries 12 are created that specify data field information within one or more original databases 22. For instance, an original dictionary 12 for an original database 22 having one or more ASCII data files may include, within an ASCII file, data field information, such as the field name, the field byte offset within an ASCII record, the field size in bytes, the field data type, key information, and the significant number of digits for floating point numbers. The field types in an original dictionary 12 include, but are not limited to, alphanumeric, integer, float, double, currency and date.

An original dictionary 12 may be created either manually or using a computer program. The present invention envisions high speed encoding, processing and decoding of data that may be defined across databases never designed to collaborate and on different computer devices anywhere over a local network, an Intranet, the Internet, or other similar network. For instance, the high speed encoding, processing and decoding of data may be defined across multiple databases including, but not limited to, inpatient, outpatient, pharmacy, radiology and physical therapy databases representing both fixed and non-fixed length records.

Optionally, the original dictionary 12 may be used to specify only a subset of the data fields within an original database 22 that are to be used in the encoding and decoding processing. The remaining fields in the original database would be excluded from the encoding and decoding processing, thereby reducing processing demands and storage requirements.

As shown at block 40 of FIG. 1, one or more encoded dictionaries 42 are created. Each encoded dictionary 42 specifies data field information within one or more encoded databases 52. Similar to the original dictionary 12, the encoded dictionary 42 may be defined in an ASCII file or a database schema. Further, the field types in an encoded dictionary 42 include, but are not limited to, alphanumeric, integer, float, double, currency and date. An encoded dictionary 42 may be created either manually or using a computer program.

An encoded dictionary 42 may be configured as a table for each of the data fields and associated information, as follows:

(1) overflow—a data value having an overflow value results in real data value being fetched from an external location, such as another file;

(2) definition—if non-zero, this variable is associated with a definition file. This file consists of all the titles, names or descriptions for the codes;

(3) word—a database record is made up of unsigned integers of 32 bits. The word indicates which word in the record contains the data field;

(4) bits—the number of bits required to contain the data field value;

(5) decimals—applies only to floating point numbers. The number of decimals places in the value;

(6) shift—the number of bits needed to shift a binary value to the right before masking in order to extract the value; and (7) baseline—for data type "date" it is the baseline. For all other types of data, it serves other purposes.

For instance, FIG. 10 shows an encoded dictionary file 42A configured as a table according to an embodiment of the present invention. The encoded dictionary file 42A includes data field information that specifies the binary structure of a encoded dictionary file 42A. The data field information includes columns for each of the data fields including, but not limited to, specifying the field name 230, the field right-bit shift offset 242 within a binary word 236, the field size in bits 238, the field data type 246, key information 248, and the significant number of digits 240 for floating point numbers. For example, the binary DRG data field 250 in the encoded dictionary file 42A is located one bit (242) from the rightmost word boundary of the third word (236) and has a size of ten bits (238).

Figure 2:
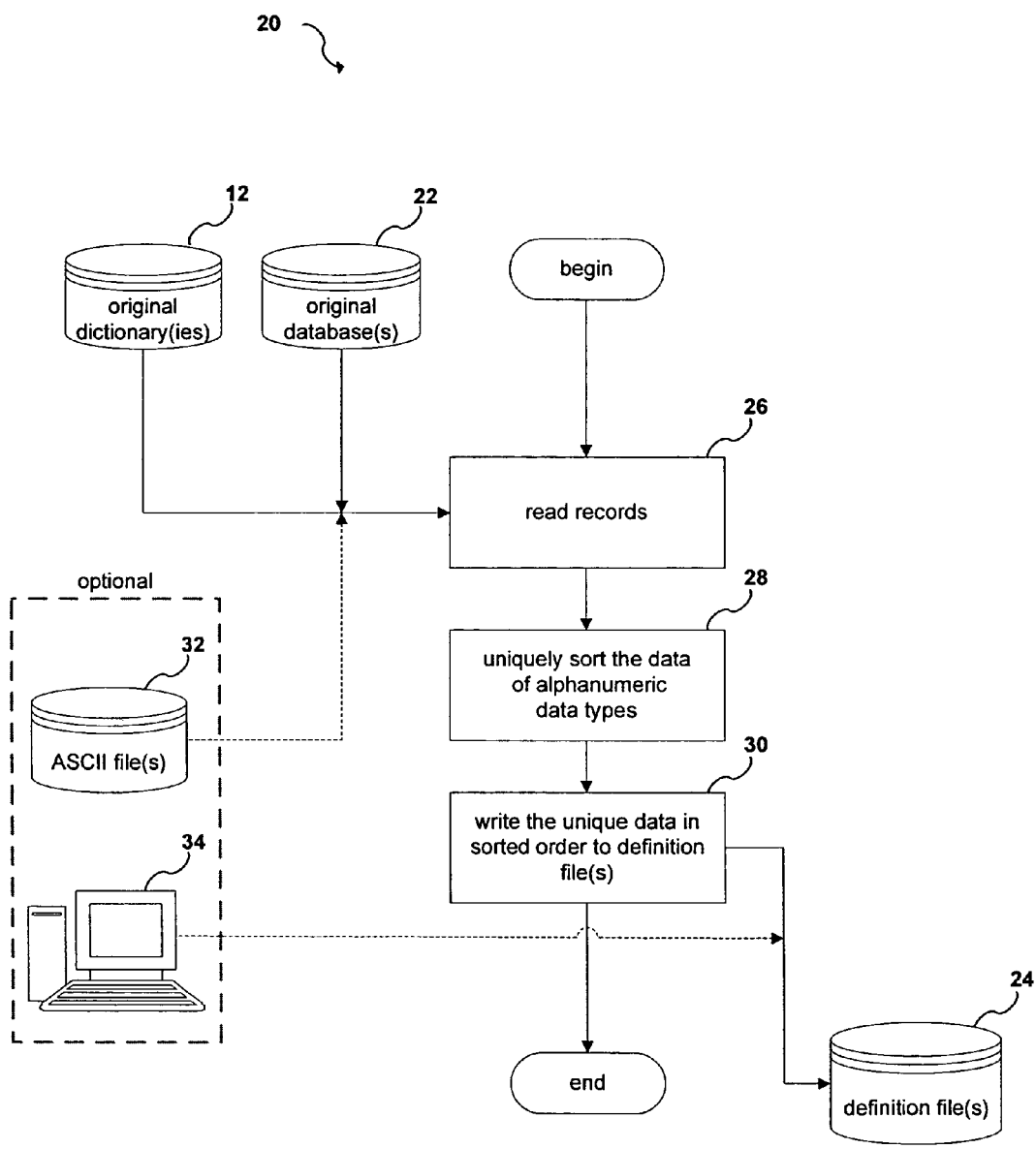
FIG. 2 is a flow chart illustrating creating definition files that specify distinct textual information relative to data defined as an alphanumeric data type according to an embodiment of the present invention.

Referring to FIG. 2, a flow chart illustrating creating definition files that specify distinct textual information relative to data values defined as an alphanumeric data type according to an embodiment of the present invention is shown. Generally, a separate encoded definition file 24 is created containing the sorted unique data values for each data field having an alphanumeric data type. More specifically, as shown at block 26, the records from one or more original databases 22 are read, and the data values having an alphanumeric data type, as defined by a corresponding one or more original dictionaries 12, are extracted from the records of the original databases 22. As shown at block 28, those data values are then uniquely sorted into a predefined order, such as an ascending sort order, with all duplicates removed. The uniquely sorted data values are then written to the one or more definition files 24, as shown at block 30. FIG. 14 shows portions of example Diagnosis 24A and DRG 24B definition files.

Optionally, one or more encoded dictionaries 24 may be created manually using any commercially available ASCII text editor 34. Further, one or more ASCII files 32 may be created by any means and then read as records at block 26 instead of using the one or more original databases 22.

Figure 3:
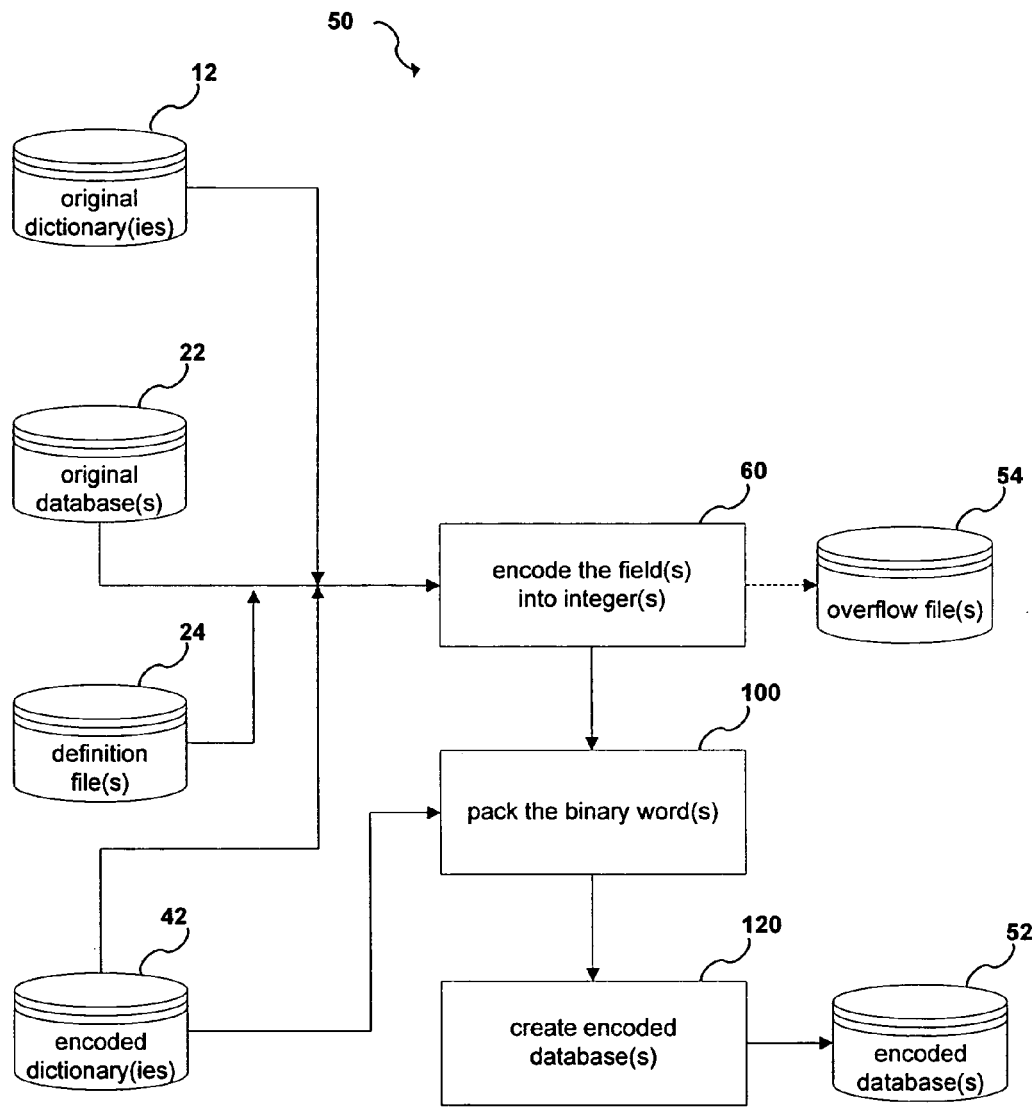
FIG. 3 is a flow chart illustrating creating an encoded database according to an embodiment of the present invention.

Referring to FIG. 3, a flow chart illustrating creating an encoded database according to an embodiment of the present invention is shown. One or more encoded databases 52 are created by encoding one or more data fields read from the one or more original databases 22 into one or more integers, as shown generally at block 60 of FIG. 3 and discussed in detail below with reference to FIG. 4. Next, the one or more data fields are packed into one or more words, as shown generally at block 100 of FIG. 3 and discussed in detail below with reference to FIG. 5. The integer data values and the associated encoded binary size (m) of that data field are used to pack the integer values in binary form into words, such as 32-bit words. This is carried out by means of shift and bitwise operations. Notably, the use of a 32-bit word is merely illustrative and is not intended to limit the size of a word. Rather a word may work equally as well with other sizes including but not limited to 16-bit, 64-bit and 128-bit words. Finally, the one or more packed words are written to one or more encoded databases 52, as shown at block 120.

Figure 4:
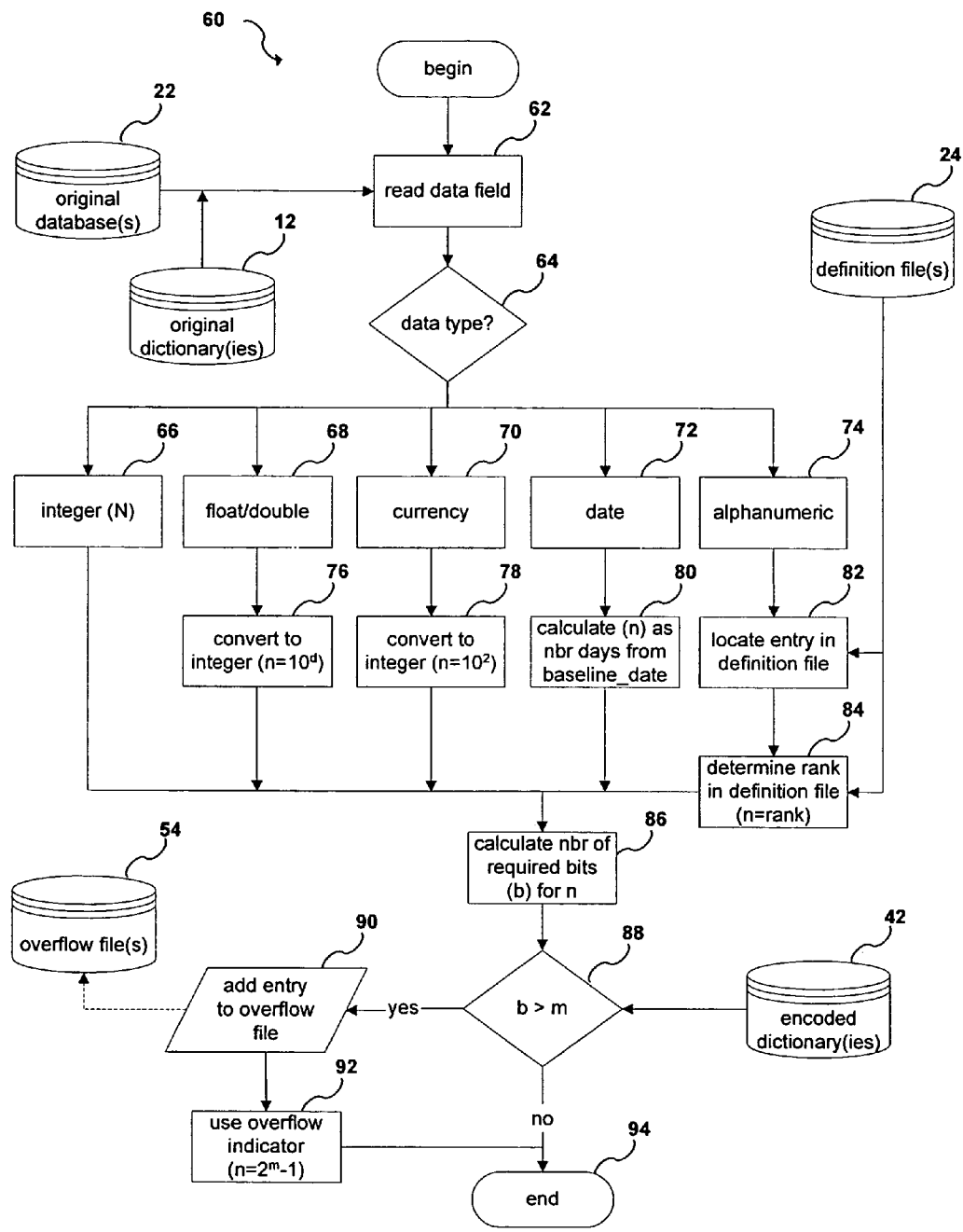
FIG. 4 is a flow chart illustrating encoding data fields into integers according to an embodiment of the present invention.

Referring to FIG. 4, a flow chart illustrating encoding data fields into integers according to an embodiment of the present invention is shown. As shown at block 62, data values of data fields, specified by one or more original dictionaries 12, are read from the one or more original databases 22. As previously discussed, the field types in an original dictionary 12 include, but are not limited to, alphanumeric, integer, float, double, currency and date. Thus, the data values of data fields having different data types are read from the one or more original databases 22.

Generally, each data value of a data field is mapped to an integer value in a collection of integers. The number of integers in the collection of integers is equal to the number of distinct data values in the given data field. Obviously, there are differences in converting data values of different data types to integer values. Therefore, the data type for the data field is determined at logic block 64. For purposes of illustration, five data types comprising integer 66, float/double 68, currency 70, date 72 and alphanumeric 74 are shown. The data value of a data field having an alphanumeric data type 74 may represent a code for particular diagnosis or medical procedure. Other data values having numerical data types may be converted to a corresponding integer value, as shown in blocks 76-80. It is to be understood, however, that the invention could readily be used with other data types as well representing both medical and non-medical related data.

More specifically, as shown at block 76, a data value having a float/double data type is converted to an integer value (n), by multiplying the data value by $10^d$, where d is the number of significant decimal places. Similarly, a data value having a currency data type is converted to an integer value by multiplying the data value by $10^2$, as shown at block 78. Further, a data value having a date data type is converted to an integer value by calculating the number of days between the data value date and a prior pre-determined base line date, such as 01/01/YYYY, as shown at block 80.

Additionally, as shown at block 82, an entry is located in one or more definition files 24 that matches the data value of a data field having an alphanumeric data type. For each data value, an integer value is determined that represents the absolute sorted position ("rank") in relation to other members of the data field. More specifically, as shown at block 84, the data value is set to the rank which represents the absolute record offset from the beginning one of the definition files 24. Thus, the data value of an alphanumeric data field is mapped to an integer value in a distinct integer collection of the same rank in its ascending order.

After all data values in a data field have been converted to integer values, the minimum number of bits required to hold or represent each integer value in binary form is determined, as shown at block 86. The minimum number of bits required to hold or represent a particular data value in binary form (b) is computed as $X \geq LogN/Log2$, where (N) is the largest number in the corresponding integer collection. Optimally, X is the lowest number that meets this condition. As shown at logic block 88, if the minimum number of bits (b) is greater than the encoded binary size (m) of that data field, as specified in one of the encoded dictionaries 22, then an that entry is added to one or more overflow files 54, as shown at block 90. Further, as shown at block 92, the data value (n) is set equal to the $(2^m-1)$, where (m) is the encoded binary size of that data field. If the minimum number of bits (b) is not greater than the maximum number of bits (m) allocated for that data field, then processing continues 94.

Figure 5:
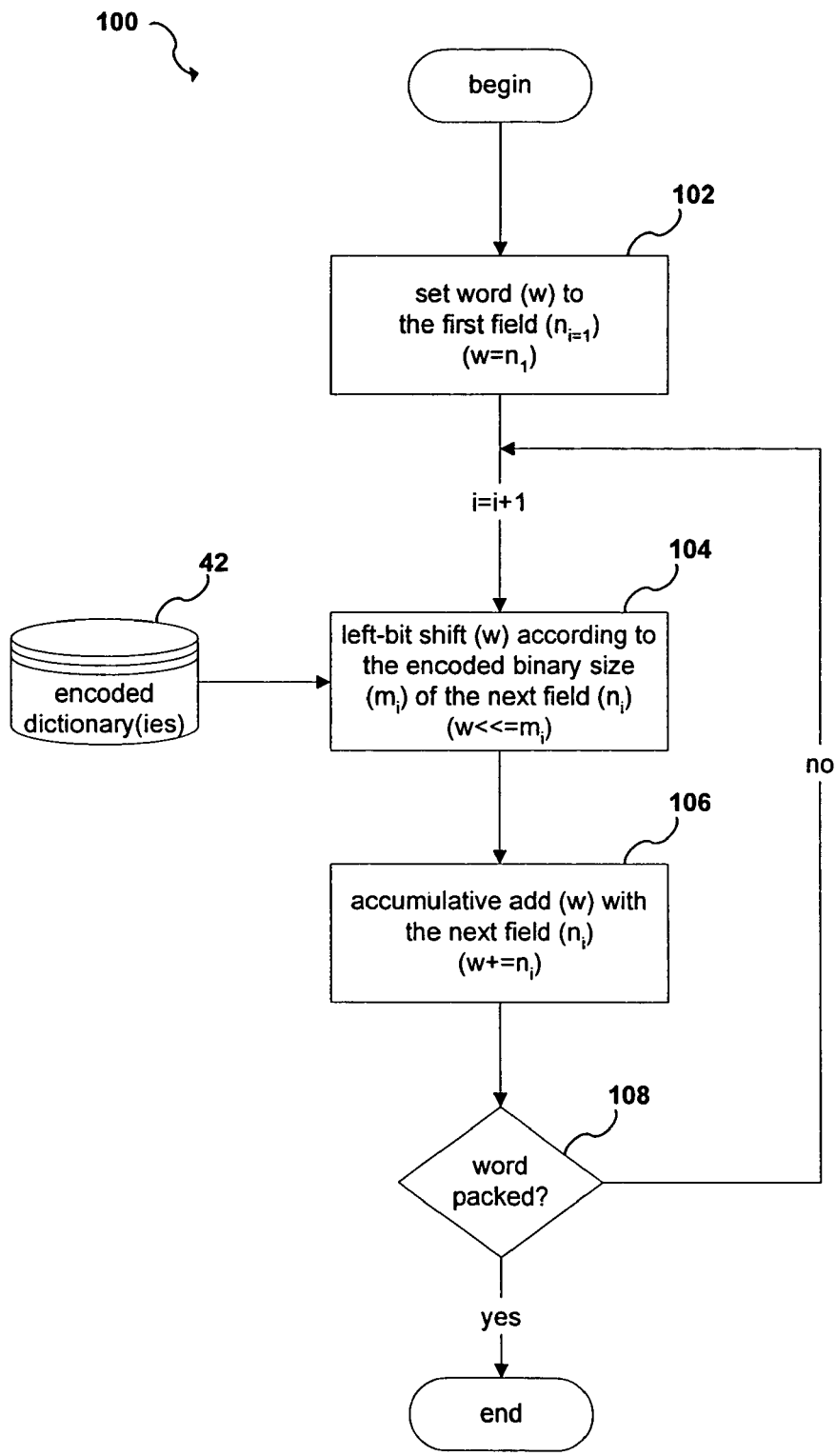
FIG. 5 is a flow chart illustrating packing binary words according to an embodiment of the present invention.

Referring to FIG. 5, a flow chart illustrating packing binary words according to an embodiment of the present invention is shown. As shown at block 102, a 32-bit word (w) is initialized with the data value ($n_1$) of the first data field. As shown at block 104, the 32-bit word is then left-bit shifted according to the encoded binary size of the next data field, as specified in one of the encoded dictionaries 42. An accumulative add is then performed on the word with the data value of the next data field, as shown at block 106. This continues until the word is packed, as shown at logic block 108.

Referring to FIG. 11, an example of packing a binary word according to an embodiment of the present invention is shown. Data fields corresponding to Diagnosis Related Group (DRG), Diagnosis3 and Length of Stay (LengthOfStay) are shown on lines 260-264, respectively. The data field for the Diagnosis3 category (25000), shown on line 262, is a numeric code used to represent diabetes. Assuming there are a total number of 15535 data values in the Diagnosis3 data field, then 14 bits are needed to represent any data value contained therein. For example, if the data value (25000), shown on line 262, is ranked as the 2,452nd data value in the Diagnosis3 data field, then it is represented by the integer value 2452. The right hand entry of line 262 shows the 14-bit binary form (00100110010100) of the integer value 2452.

Similarly, the data value for the DRG data field (243) is shown in its 10-bit binary form (0011110011), as shown on line 260. Further, the data value for the Length of Stay data field (84 days) is also shown in its binary form (01010100), as shown on line 264.

As shown on line 266, the binary form of the data value for the Diagnosis3 data field is positioned as the 14 right-most bits of a 32-bit word (word=Diagnosis3). The word is then shifted to the left by 10 bits (word <<=10), as shown on line 268. The binary form of the data value for the DRG data field is then inserted as an accumulative add to the 10 right-most bits of the 32-bit word (word +=DRG), as shown on line 270. The 32-bit word containing the binary forms of the data values for the Diagnosis3 data field and DRG data field is then shifted to the left by 8 bits (word <<=8), as shown on line 272. Finally, the binary form of the data value for the Length of Stay (LengthOfStay) data field is then inserted as an accumulative add to the 8 right-most bits of the 32-bit word, as shown on line 274.

Figure 6:
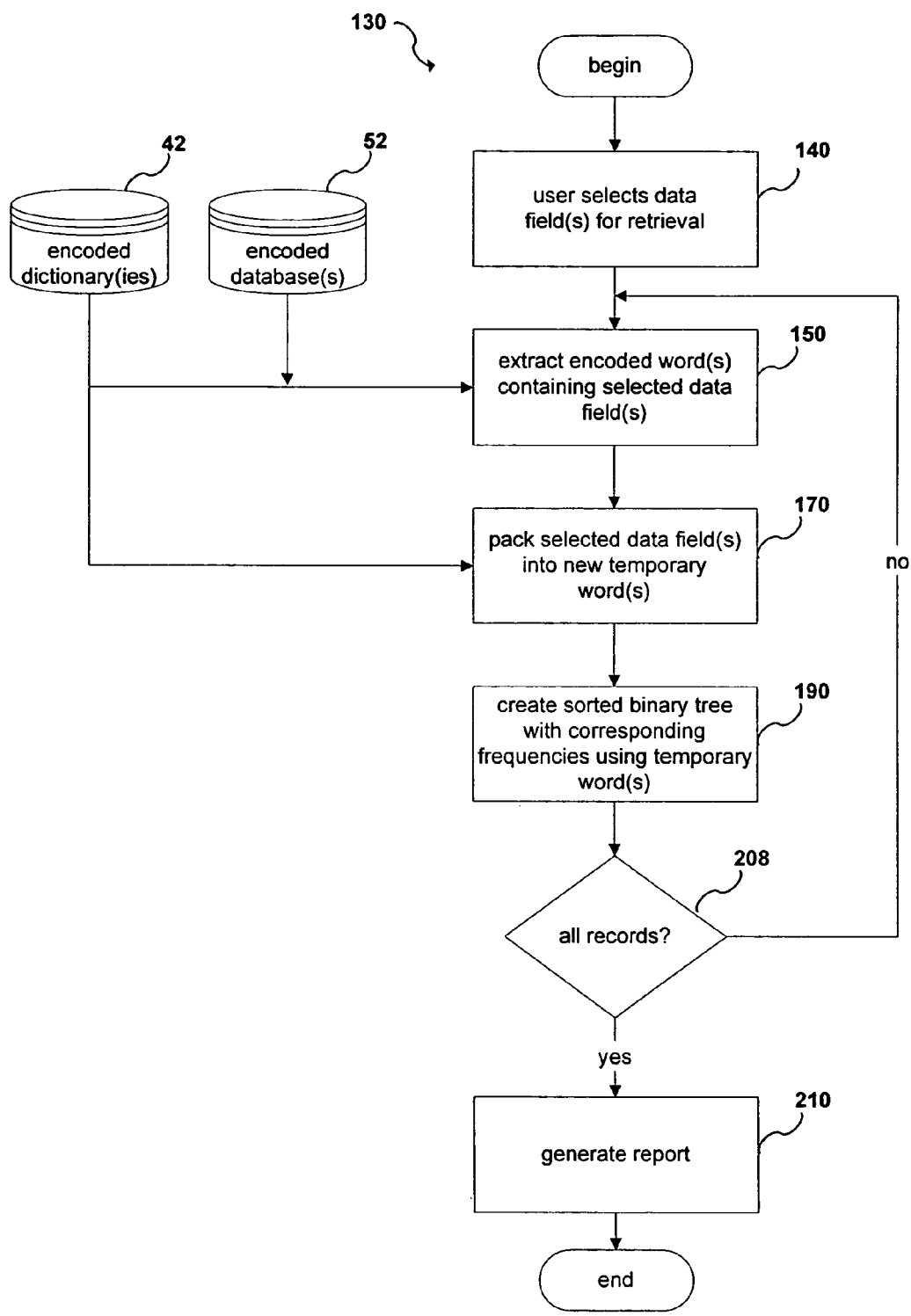
FIG. 6 is a flow chart illustrating retrieving records according to an embodiment of the present invention.

Referring to FIG. 6, a flow chart illustrating retrieving records according to an embodiment of the present invention is shown. Initially, as shown at block 140, data fields are selected or specified for retrieval from one or more encoded databases 52. Selection of one or more selected data fields for retrieval may either be done manually or using a user interface. Typically, the selected or specified data fields will be information required to generate a particular report. Also, different specified data fields will frequently be stored (in their respective encoded forms) in different packed words, such as 32-bit words. The selected data fields are extracted from one or more words, as shown generally at block 150 of FIG. 6 and discussed in detail below with reference to FIG. 7. The selected data fields are then packed into one or two binary form temporary words, as shown at block 170, used as input parameters to a binary tree algorithm function, as shown generally at block 190 of FIG. 6 and discussed in detail below with reference to FIG. 8. Packing the variables into one or two words takes less memory for the binary tree algorithm function. As such, any of following may be used as input parameters to the binary tree algorithm function:

(1) no dependent variables and all independent variables are encoded into one 32-bit word and passed as a single parameter;

(2) no dependent variables and all independent variables are encoded into two 32-bit words and passed as two parameters;

(3) one or more dependent variables and all independent variables are encoded into one 32-bit word and passed as a single parameter; or (4) one or more dependent variables and all independent variables are encoded into two 32-bit words and passed as two parameters.

A sorted binary tree is created with corresponding frequencies using the one or two temporary words, as shown generally at block 190 of FIG. 6 and discussed in detail below with reference to FIG. 8. As shown at logic block 208, processing continues until all records have been processed. Finally, a report is generated based upon the selected data fields, as shown generally at block 210 of FIG. 6 and discussed in detail below with reference to FIG. 9.

Figure 7:
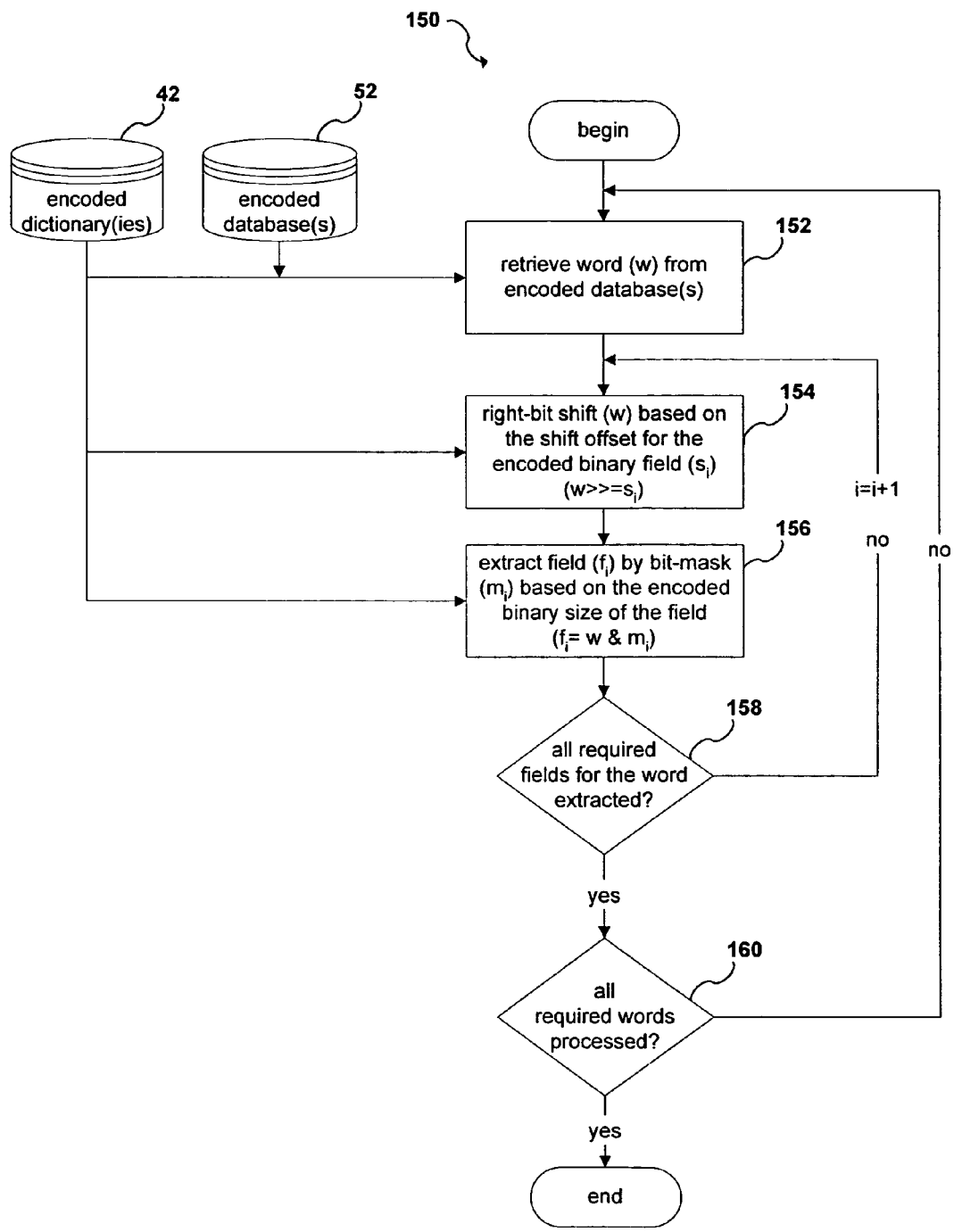
FIG. 7 is a flow chart illustrating extracting encoded words containing selected data fields according to an embodiment of the present invention.

More specifically, referring to FIG. 7, a flow chart illustrating extracting encoded words containing selected data fields according to an embodiment of the present invention is shown. As shown at block 152, a word containing a selected data field, as specified by one of the encoded dictionaries 42, is retrieved from one of the encoded databases 52. The word is right-bit shifted according to the shift offset for the encoded binary field, as shown at block 154. Next, as shown at block 156, the selected data field is extracted from the word using a bit-mask calculated from the encoded binary size of that data field. For instance, as shown in FIG. 10, a word containing a data value of a Diagnosis3 data field 252 is right-bit shifted by 18 bits according to the shift offset 242. The data value of the Diagnosis3 data field is then extracted by bit-masking the word with $(2^{14}-1)$, where 14 represents the encoded binary size in bits 238 of the Diagnosis3 data field 252. Processing then continues for all selected data fields in all words containing the selected data fields, as shown at logic blocks 158 and 160 of FIG. 7.

FIG. 12 shows an example of extracting data fields from a binary word according to an embodiment of the present invention. In this example, the Diagnostic3, DRG and Length of Stay (LengthOfStay) data values are extracted from a 32-bit word (word) using bitwise and mask operations, as shown at lines 282-294. Mask1 276, mask2 278 and mask3 280 comprise 14-bit, 10-bit, and 8-bit binary masks, respectively, shown in binary forms.

As shown on lines 284 and 286, the LengthOfStay portion (bits 0-7) of the original 32-bit word shown on line 282 is extracted. The original 32-bit word shown on line 282 is right-bit shifted by 0 bits as shown on line 284. Next, the resulting 32-bit word is ANDed with mask3 280, thereby removing the bits that are not contained in both the right shifted 32-bit word and mask3 280. Thus, mask3 280 is used to remove the leftmost 24 bits from the resulting 32-bit word while keeping the rightmost 8 bits, thereby extracting the LengthOfStay portion of the 32-bit word (bits 0-7 of the original 32-bit word shown on line 282).

Next, as shown on lines 288 and 290, the DRG portion (bits 8-17) of the original 32-bit word shown on line 282 is extracted. The original 32-bit word shown on line 282 is right shifted by 8 bits, as shown on line 288. Thus, the LengthOfStay portion of the original 32-bit word is removed. Next, the resulting 32-bit word is ANDed with mask2 278, thereby removing the bits that are not contained in both the right-bit shifted 32-bit word and mask2 278, as shown on line 290. Thus, mask2 278 is used to remove the leftmost 22 bits from the right shifted 32-bit word while keeping the rightmost 10 bits, thereby extracting the DRG portion of the 32-bit word (bits 8-17 of the original 32-bit word shown on line 282).

Next, as shown on lines 292 and 294, the Diagnosis3 portion (bits 18-31) of the original 32-bit word shown on line 282 is extracted. The original 32-bit word shown on line 282 is right shifted by 18 bits, as shown on line 292. Thus, the LengthOfStay and DRG potions of the original 32-bit word are removed. Next, the resulting 32-bit word is ANDed with mask1 276, thereby removing the bits that are not contained in both the right-bit shifted 32-bit word and mask1 276, as shown on line 294. Thus, mask1 276 is used to remove the leftmost 18 bits from the right-bit shifted 32-bit word while keeping the rightmost 14 bits, thereby extracting the Diagnosis3 portion of the 32-bit word (bits 18-31 of the original 32-bit word shown on line 282). However, in this example, mask1 276 is not necessary to extract the data value for the Diagnosis3 data field because the LengthOfStay and DRG potions of the original 32-bit word were previously removed leaving only the Diagnosis3 portion after the original 32-bit word was right-bit shifted by 18 bits.

Figure 8:
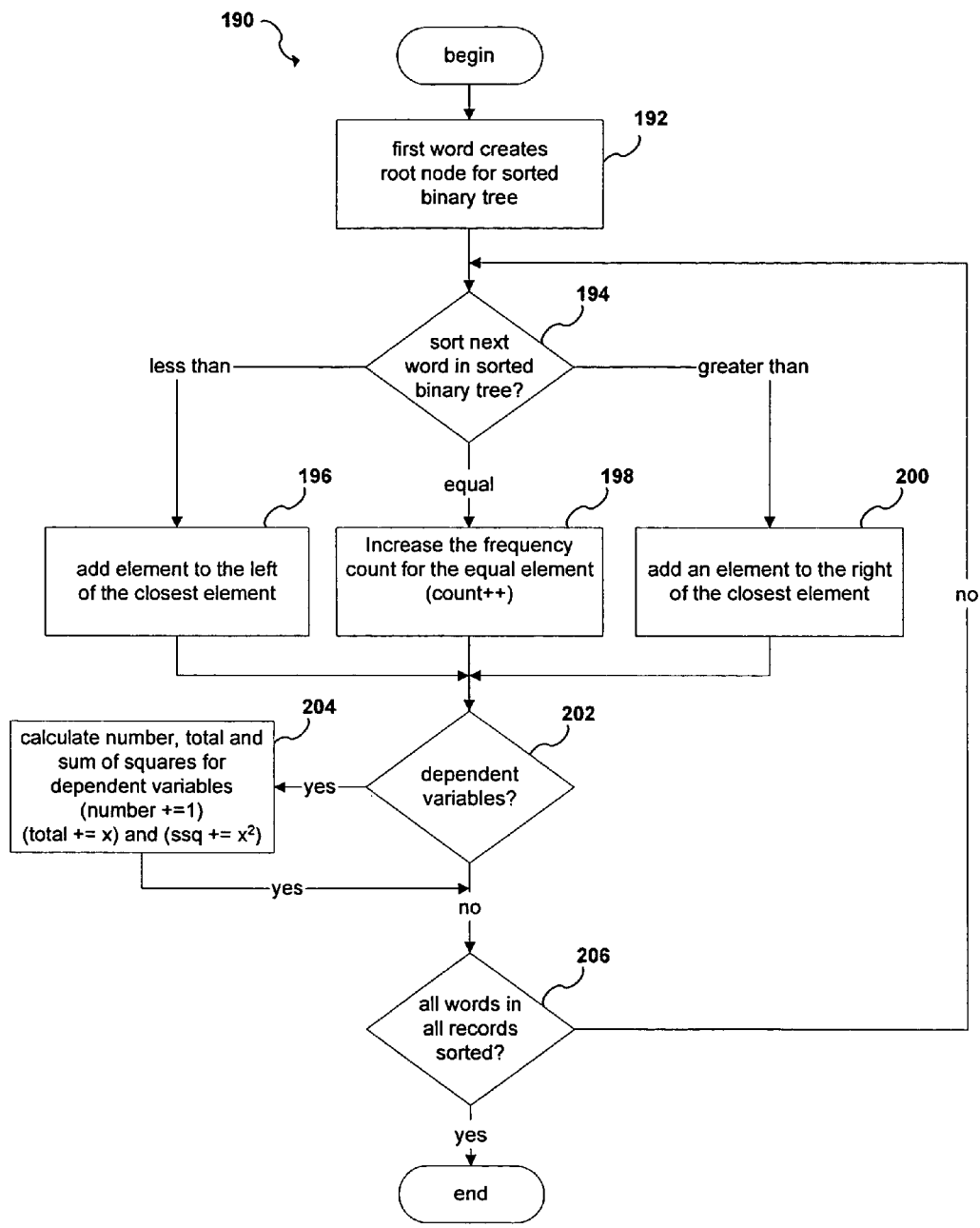
FIG. 8 is a flow chart illustrating creating a sorted binary tree according to an embodiment of the present invention.

Referring to FIG. 8, a flow chart illustrating creating a sorted binary tree according to an embodiment of the present invention is shown. One or two new temporary binary form words are used as input parameters to a binary tree algorithm. In particular, as shown at block 192, the first word that is input into the binary tree algorithm creates the root node for a sorted binary tree. Each successive word is uniquely sorted as appropriate in the sorted binary tree, as shown at logic block 194 and blocks 196 and 200. As shown at block 198, if the successive word is not unique, then a frequency count is incremented. Next, a determination is made as to whether there are any associated dependent variables, at logic block 202. If there are associated dependent variables, then the number (number +=1), a total (total +=x) and a sum of squares (ssq+ =$x^2$) are accumulated for the dependent variables, as shown at block 204, where (x) is the data value of the selected data field. As shown at logic block 206, processing continues until all words in all records are sorted.

Figure 9:
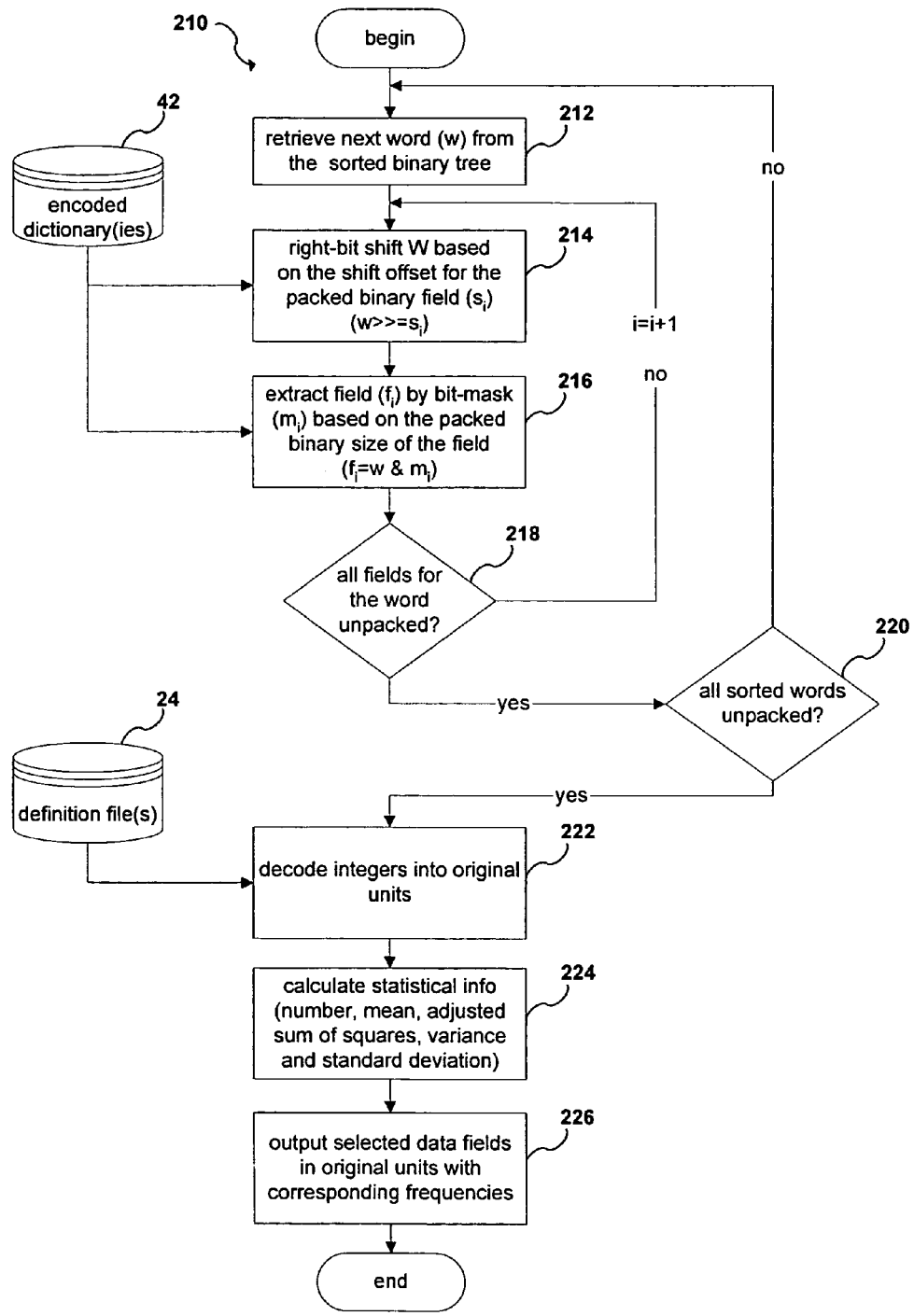
FIG. 9 is a flow chart illustrating generating a report according to an embodiment of the present invention.

Referring to FIG. 9, a flow chart illustrating generating a report according to an embodiment of the present invention is shown. As shown at block 212, a word is retrieved form the sorted binary tree. The word is right-bit shifted according to the shift offset for the encoded binary field, as shown at block 214. Next, as shown at block 216, the selected data field is extracted from the word using a bit-mask calculated using the encoded binary size of that data field. As shown at logic blocks 218 and 220, processing continues for all data fields in all words. The binary form integer values are then decoded to provide data values in their original units, statistical information is calculated, and the results are output to an ASCII text file or formatted output file for use in generating the desired report, as shown at blocks 222-226, respectively. Statistical information may include, but is not limited to, the number (n), the adjusted sum of squares (assq=ssq−(total$^2$/n)), variance (v=assq/(n−1)), mean (m=total/n) and standard deviation (sd=$\sqrt{v}$). For instance, FIG. 13 shows an example of a generated report outputting covered charges for Medicare inpatients by sex and age.

As an example demonstrating the successive steps for retrieving stored data from one or more encoded databases 52, assume that a report needs to be generated that shows the number of patients with or without surgery by discharge status and sex at a particular hospital. Further, assume that the Surgery Indicator, Discharge Status and Gender data fields are selected. These types of data fields are considered to be independent variables. Data values from each of these data fields are successively extracted, record by record, and packed into new binary words, as previously discussed with reference to FIG. 7. These words are then used as input parameters to the binary tree algorithm, as previously discussed with reference to FIG. 8. In the binary tree algorithm each unique Surgery Indicator/Discharge Status/Gender combination generates a distinct level for output and one count is added for that level each time a new binary word matches it. After all the records in one or more of the encoded databases 52 have been processed, the count frequency for each unique Surgery Indicator/Discharge Status/Gender combination may be used to provide the desired information for the report.

Other data fields, such as Hospital Length of Stay and Currency Amounts, are referred to as dependent variables because they are used to compute statistics, such as number, mean, total and standard deviation. Dependent variable data fields are extracted from the binary words stored in one or more encoded databases 52, record by record, and then stored in a structure which is appended to the packed independent variable parameter words, as previously discussed with reference to FIGS. 6-8. Generally, the binary tree algorithm can accumulate frequencies and/or statistics for all combinations of data values, as previously discussed with reference to FIG. 8.

After all of the records in one or more of the encoded databases 52 have been processed, a binary tree algorithm is used to produce packed parameter words, their respective frequencies and associated statistics. The encoded data values, that is, integers in binary form, are unpacked from the parameter words using shifting and masking operations. The binary form integer values are then decoded to provide data values in their original units, and outputted to an ASCII text file or formatted output file for use in generating the desired report.

The present invention thus includes a computer program which may be hosted on a storage medium and includes instructions which perform the processes set forth in the present specification. The storage medium can include, but is not limited to, any type of disk including floppy disks, optical disks, CD-ROMs, magneto-optical disks, ROMs, RAMs, EPROMs, EEPROMs, flash memory, magnetic or optical cards, or any type of media suitable for storing electronic instructions.

Obviously, many other modifications and variations of the present invention are possible in light of the above teachings. The specific embodiments discussed herein are merely illustrative, and are not meant to limit the scope of the present invention in any manner. It is therefore to be understood that within the scope of the disclosed concept, the invention may be practiced otherwise than as specifically described.

The invention claimed is:

1. A method for processing data having a plurality of data values of a plurality of data fields of varying types and lengths, comprising:
   encoding each of the plurality of data values into a corresponding one of a plurality of integer values based on the respective type of the data field;
   determining an optimum bit length for each of the plurality of data fields, wherein each optimum bit length is substantially equal to log N/log 2, where N is the largest integer value corresponding to the respective data field;
   packing and storing binary forms of differing two or more of the plurality of integer values into distinct first binary portions of a corresponding one of a plurality of first binary words, wherein each distinct first binary portion has a bit length equal to the optimum bit length of the corresponding data field;
   selecting one or more of the plurality of data fields;
   unpacking each of the distinct first binary portions corresponding to the selected one or more data fields into a corresponding one of a plurality of unpacked integer values;
   packing binary forms of each of differing two or more of the plurality of unpacked integer values into distinct second binary portions of a corresponding one of a plurality of second binary words;
   employing each of the plurality of second binary words as an input parameter to a selected function to derive output information collectively representing the data values of the selected one or more data fields; and
   displaying the output information to a user.

2. The method of claim 1, wherein the selected function comprises a binary tree algorithm function.

3. The method of claim 1, wherein one or more of the selected one or more data fields comprise independent variable data fields, and the combining comprises combining unpacked integer values of encoded data values of the independent variable data fields to form the plurality of second binary words.

4. The method of claim 3, wherein one or more of the selected one or more data fields comprise dependent variable data fields, and unpacked integer values corresponding to the dependent variable data fields are respectively appended to the plurality of second binary words.

5. The method of claim 3, wherein formation of the plurality of second binary words includes encoding no dependent variable data fields and all independent variable data fields into one or two 32-bit words.

6. The method of claim 3, wherein formation of the plurality of second binary words includes encoding one or more dependent variable data fields and all independent variable data fields into one or two 32-bit words.

7. The method of claim 1, wherein the plurality of first binary words are formed from respective binary forms of the integer values by means of bitwise and shifting operations.

8. The method of claim 7, wherein the data fields are of varying length, and all of the plurality of first binary words are of the same selected length.

9. The method of claim 8, wherein all of the plurality of first binary words have a length of 32 bits.

10. The method of claim 1, wherein the unpacking integer values includes extracting binaries respectively representing integer values that are to be unpacked by means of bitwise and masking operations.

11. The method of claim 1, wherein the data is contained in a database.

12. The method of claim 11, wherein the database comprises one or more flat ASCII text files.

13. A method for encoding a plurality of data values of a corresponding plurality of data fields of varying types and lengths, wherein at least one of the plurality of data fields is different in at least one of a type and a length from at least another of the plurality of data fields, comprising:
    mapping each of the plurality of data values to an integer value of a corresponding plurality of integers based on the respective type of the data field;
    representing each of the plurality of integer values in a corresponding one of the plurality of integers in a binary form having a bit length is substantially equal to log N/log 2, where N is the largest integer value corresponding to the respective data field;
    combining differing two or more of the binary forms in a corresponding one of a plurality of binary words, wherein each of the plurality of binary words are of the same specified length, and the binary forms contained in at least one of the plurality of binary words represents data values selected from different data fields; and
    displaying output information to a user based on the plurality of binary words.

14. The method of claim 13, wherein the bit length of the binary forms representing the integer value in the one of the plurality of integers is equal to the minimum bit length required to represent the largest integer value in the one of the plurality of integers.

15. The method of claim 14, wherein the integer values in at least one of the plurality of integers are consecutively numbered in ascending order starting from zero.

16. The method of claim 13, wherein the bit length of the binaries representing integer values of the one of the plurality of integers is a number that is greater than or equal to log N/log 2, where N is the largest integer value in the one of the plurality of integers.

17. The method of claim 16, wherein each of the plurality of binary words are each 32 bits in length.

18. The method of claim 13, wherein the data values of at least one of the plurality of data fields comprise numerical values.

19. The method of claim 13, wherein the data values of at least one of the plurality of data fields comprise alphanumeric codes, each alphanumeric code representing a different one of a plurality of items.

20. The method of claim 13, wherein the plurality of data fields comprise different categories of information contained in a set of medical records.

21. A computer storage medium for processing data having a plurality of data values of a plurality of data fields of varying types and lengths, comprising:
    a first computer code for encoding each of the plurality of data values into a corresponding one of a plurality of integer values based on the respective type of the data field;
    a second computer code for determining an optimum bit length for each of the plurality of data fields, wherein each optimum bit length is substantially equal to log N/log 2, where N is the largest integer value corresponding to the respective data field;
    a third computer code for packing and storing binary forms of differing two or more of the plurality of integer values into distinct first binary portions of a corresponding one of a plurality of first binary words, wherein each distinct first binary portion has a bit length equal to the optimum bit length of the corresponding data field;
    a fourth computer code for selecting one or more of the plurality of data fields;
    a fifth computer code for unpacking each of the distinct first binary portions corresponding to the selected one or more data fields into a corresponding one of a plurality of unpacked integer values;
    a sixth computer code for packing binary forms of each of differing two or more of the plurality of unpacked integer values into distinct second binary portions of a corresponding one of a plurality of second binary words;
    a seventh computer code for employing each of the plurality of second binary words as an input parameter to a selected function to derive output information collectively representing the data values of the selected one or more data fields; and
    an eight computer code for displaying the output information to a user.

22. The computer storage medium of claim 21, wherein the selected function comprises a binary tree algorithm function.

23. The computer storage medium of claim 22, wherein the plurality of first binary words are formed from respective binary forms of integer values by means of bitwise and shifting operations.

24. The computer storage medium of claim 22, wherein the plurality of first binary words are formed from respective binary forms of integer values by means of bitwise and shifting operations.

25. The computer storage medium of claim 21, wherein the data is contained in a database.

26. The computer storage medium of claim 25, wherein the database comprises one or more flat ASCII text files.

27. A computer system for processing data having a plurality of data values of a corresponding plurality of data fields of varying types and lengths, comprising:

a processor; and a computer readable medium connected to the processor, the computer-readable medium including processor instructions configured to be read by the processor and to thereby cause the processor to:

encode each of the plurality of data values into a corresponding one of a plurality of integer values based on the respective type of the data field;

pack and store binary forms of differing two or more of the plurality of integer values into distinct first binary portions of a corresponding one of a plurality of first binary words, wherein each distinct first binary portion has a bit length equal to an optimum bit length of the corresponding data field wherein the optimum bit length is substantially equal to log N/log 2, where N is the largest integer value corresponding to the respective data field;

select one or more of the plurality of data fields;

unpack each of the distinct first binary portions corresponding to the selected one or more data fields into a corresponding one of a plurality of unpacked integer values;

pack binary forms of each of differing two or more of the plurality of unpacked integer values into distinct second binary portions of a corresponding one of a plurality of second binary words;

employ each of the plurality of second binary words as an input parameter to a selected function to derive output information collectively representing the data values of the selected one or more data fields; and display the output information to a user.

* * * * *